(12) United States Patent
Spergel et al.

(10) Patent No.: US 11,884,650 B2
(45) Date of Patent: Jan. 30, 2024

(54) SUBSTITUTED HETEROCYCLIC COMPOUNDS

(71) Applicant: BRISTOL-MYERS SQUIBB COMPANY, Princeton, NJ (US)

(72) Inventors: Steven H. Spergel, Warrington, PA (US); Ryan M. Moslin, Princeton, NJ (US); Michael Edward Mertzman, New Hope, PA (US)

(73) Assignee: BRISTOL-MYERS SQUIBB COMPANY, Princeton, NJ (US)

(*) Notice: Subject to any disclaimer, the term of this patent is extended or adjusted under 35 U.S.C. 154(b) by 0 days.

(21) Appl. No.: 17/743,615

(22) Filed: May 13, 2022

(65) Prior Publication Data
US 2022/0388987 A1    Dec. 8, 2022

Related U.S. Application Data

(60) Provisional application No. 63/318,508, filed on Mar. 10, 2022, provisional application No. 63/188,498, filed on May 14, 2021.

(51) Int. Cl.
*C07D 401/14* (2006.01)
*C07D 401/12* (2006.01)

(52) U.S. Cl.
CPC ......... *C07D 401/14* (2013.01); *C07D 401/12* (2013.01)

(58) Field of Classification Search
CPC .............................. C07D 401/14; C07D 401/12
See application file for complete search history.

(56) References Cited

FOREIGN PATENT DOCUMENTS

| WO | 2020/086616 A1 | 4/2020 | |
|----|----|----|----|
| WO | WO-2020086616 A1 * | 4/2020 | ........... C07D 213/74 |
| WO | 2020/092196 A1 | 5/2020 | |

* cited by examiner

*Primary Examiner* — Samira J Jean-Louis
(74) *Attorney, Agent, or Firm* — Elliott Korsen

(57) ABSTRACT

There are disclosed compounds of the following formula I:

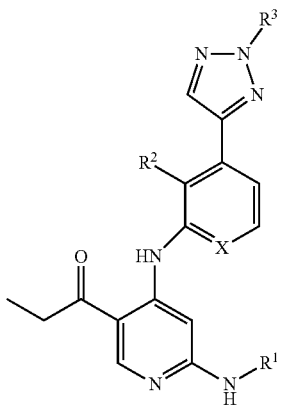

or a stereoisomer or pharmaceutically acceptable salt thereof, wherein all substituents are as defined herein, which are useful in the modulation of IL-12, IL-23 and/or IFNα, by acting on Tyk-2 to cause signal transduction inhibition. The compounds of the invention may be useful for treating neurodegenerative diseases or disorders.

6 Claims, No Drawings

SUBSTITUTED HETEROCYCLIC COMPOUNDS

CROSS-REFERENCE TO RELATED APPLICATIONS

This application claims the benefit of U.S. Provisional Application No. 63/188,498, filed May 14, 2021, and U.S. Provisional Application No. 63/318,508, filed Mar. 10, 2022, the disclosures of which are incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are -substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal. In particular, this invention relates to compounds which show utility against neurodegenerative diseases.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/0 receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

TYK2 inhibition may also be utilized in both solid tumors and hematologic malignancies both as a monotherapy and in combination with existing standards of care including immunotherapy.

Ex vivo studies in T-cell acute lymphoblastic leukemia (T-ALL) have shown that TYK2 is required for the survival of T-ALL, suggesting a potential direct cancer killing mechanism for TYK2 inhibitors in this indication, Sanda, T. et al. TYK2-STAT1-BCL2 Pathway Dependence in T-cell Acute Lymphoblastic Leukemia. *Cancer Discov.* 3, 564-577 (2013). Multiple TYK2 activating mutations in T-ALL cell lines have been detected and characterized. NPM1-TYK2 gene fusions have also been identified in a subset of cutaneous T-cell lymphomas (CTCL), and TYK2 was shown to be an oncogenic driver of transformation, Kuravi, S. et al. Functional characterization of NPM1-TYK2 fusion oncogene. *Npj Precis. Oncol.* 6, 3 (2022). Loss of TYK2 signaling could inhibit this transformational potential.

Effective TYK2 inhibitors have been described; however, these compounds tend to be highly polar compounds subject to high efflux ratios in standard efflux models, Wrobleski, S. T. et al. Highly selective inhibition of Tyrosine Kinase 2 (TYK2) for the treatment of autoimmune diseases: Discovery of the allosteric inhibitor BMS-986165. *J. Med. Chem.* 62, 8973-8995 (2019). It is well established that one pathway for multidrug resistance is increased expression of efflux transporters, Gottesman, M. M. et al. Multidrug Resistance in Cancer: Role of ATP-Dependent Transporters. *Nature Rev. Cancer* 2, 48-58 (2002), Fletcher, J. I. et al. ABC transporters in cancer: more than just drug efflux pumps. *Nature Rev. Cancer* 10, 147-156 (2010).

Therefore, compounds with lower efflux ratios in in vitro models could potentially have a greater chance of effectively treating some oncogenic indications.

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating neurodegenerative diseases, comprising administering to a host in need of such treatment a therapeutically effective amount of at least one of the compounds of the present invention.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

In a first aspect of the present invention, there is provided a compound of formula I

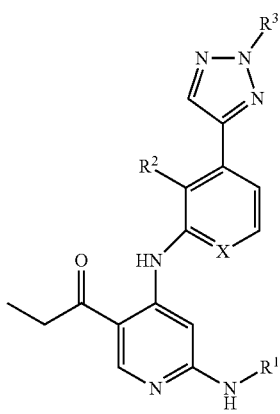

(I)

or a stereoisomer or pharmaceutically acceptable salt thereof,
wherein
X is —N— or —CH—;
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

In a second aspect of the invention, there is provided a compound of the formula

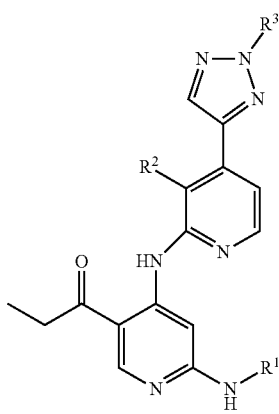

(I)

or a stereoisomer or pharmaceutically acceptable salt thereof,
wherein
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

In a 3rd aspect of the invention, there is provided a compound of the formula

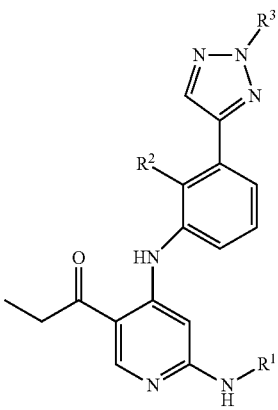

or a stereoisomer or pharmaceutically acceptable salt thereof,
wherein
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

In another aspect, there is provided a compound selected from the exemplified examples within the scope of the first aspect, or a pharmaceutically acceptable salt thereof.

In another aspect, there is provided a compound selected from any subset list of compounds within the scope of any of the above aspects.

In another aspect, there is provided a compound (IUPAC naming convention) or a pharmaceutically acceptable salt thereof, selected from
N-(4-((3-methoxy-4-(2-methyl-2H-1,2,3-triazol-4-yl)pyridin-2-yl)amino)-5-propionylpyridin-2-yl)cyclopropanecarboxamide,
N-(4-((3-methoxy-4-(2-cyclopropyl-2H-1,2,3-triazol-4-yl)pyridin-2-yl)amino)-5-propionylpyridin-2-yl)cyclopropanecarboxamide, N-(4-((2-methoxy-3-(2-methyl-2H-1,2,3-triazol-4-yl)phenyl)amino)-5-propionylpyridin-2-yl)cyclopropanecarboxamide, N-(4-((4-fluoro-2-methoxy-3-(2-methyl-2H-1,2,3-triazol-4-yl)phenyl)amino)-5-propionylpyridin-2-yl)cyclopropanecarboxamide, N-(4-((3-fluoro-2-methoxy-3-(2-methyl-2H-1,2,3-triazol-4-yl)phenyl)amino)-5-propionylpyridin-2-yl)cyclopropanecarboxamide, and N-(4-((3-methyl-2-methoxy-3-(2-methyl-2H-1,2,3-triazol-4-yl)phenyl)amino)-5-propionylpyridin-2-yl)cyclopropanecarboxamide.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating neurodegenerative disease (or use of the compounds of the present invention for the manufacture of a medicament for the treatment of said diseases), comprising administering to a patient in need of such treatment a therapeutically-effective amount of a compound of Formula I, wherein the disease is selected from as Alzheimer's disease, Parkinson's disease, ALS, Multiple Sclerosis (RMS and/or progressive MS, including CIS, optic neuritis, neuromyelitis optica).

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}<1000$ nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

One skilled in the field will understand that, when the designation "CO$_2$" is used herein, this is intended to refer to the group

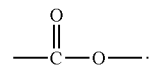

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

The term "alkoxy" refers to an oxygen atom substituted by alkyl or substituted alkyl, as defined herein. For example, the term "alkoxy" includes the group —O—C$_{1-6}$ alkyl such as methoxy, ethoxy, propoxy, isopropoxy, n-butoxy, secbutoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

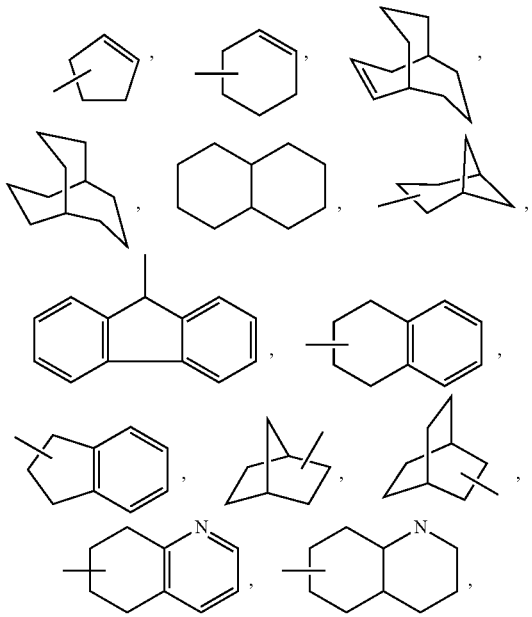

and the like, which optionally may be substituted at any available atoms of the ring(s).

Preferred cycloalkyl groups include cyclopropyl, cyclobutyl, cyclopentyl, and cyclohexyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

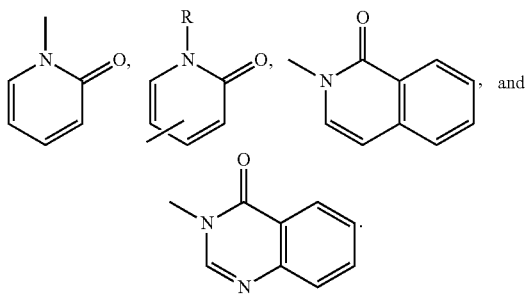

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

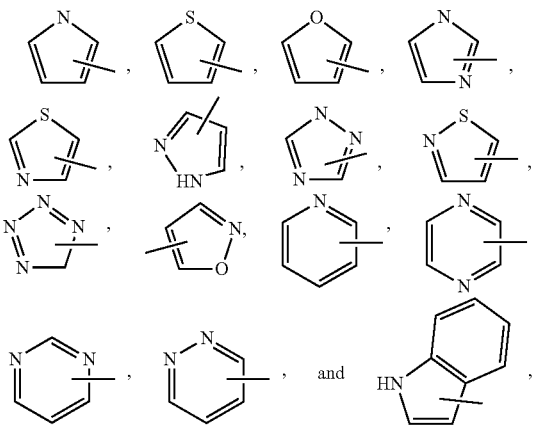

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art and are described in Rautio, J. et al., *Nature Review Drug Discovery*, 17, 559-587 (2018).

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 and/or IFNα, and particularly the selective inhibition of function of IL-23, IL-12 and/or IFNα, by acting on Tyk2 to mediate signal transduction. Such conditions include IL-23-, IL-12- or IFNα-associated diseases in which pathogenic mechanisms are mediated by these cytokines and the subsequent activation of the Tyk2 pathway with subsequent pro-inflammatory responses which may occur in the peripheral and/or central compartments.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting or slowing its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and/or IFNα-stimulated cellular responses, compounds of Formula I are useful in treating IL-23-, IL-12- and/or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, Multiple Sclerosis (RMS and/or progressive MS, including CIS, optic neuritis, neuromyelitis optica), cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, Multiple Sclerosis (RMS and/or progressive MS, including CIS, optic neuritis, neuromyelitis optica), cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Alzheimer's disease, Parkinson's disease, ALS, Multiple Sclerosis (RMS and/or progressive MS, including CIS, optic neuritis, neuromyelitis optica), When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release.

Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

The key intermediates shown in Figure 1 can be assembled to give compound 1 in a variety of ways known to one skilled in the art of synthetic organic chemistry.

FIG. 1

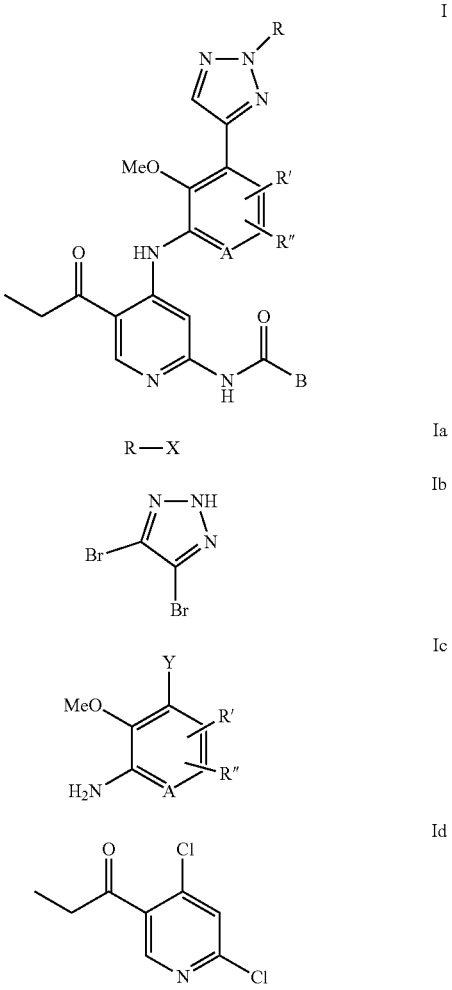

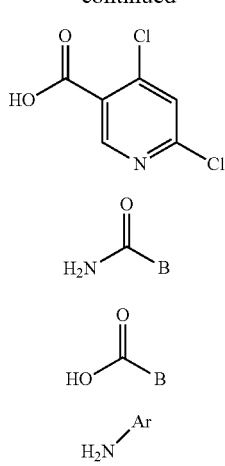

Scheme 1 shows how intermediate Ia, where X=halogen, such as iodide, in the cases where R=simple alkyl (methyl, ethyl, etc) and intermediate Ib can be combined in the presence of an appropriate base, preferably potassium carbonate, in an appropriate solvent, preferably DMF to give intermediates of formula II. In the case where R=cyclopropyl, Ib can be treated with cyclopropylboronic acid in the presence of copper (II) acetate, 2,2'-bipyridine and sodium carbonate in dichloroethane at elevated temperatures. II can then be mono-debrominated in the presence of a strong reducing base, particularly isopropylmagnesium bromide, THF solution in ether at low temperature to give intermediates of formula IIa. II can also be used, as is, to make more highly substituted 1,2,3-triazoles. IIa can be used, as is, or can be converted to the corresponding boronic acid (IIb) a metal halogen exchange followed by quenching with a trialkylborate, specifically trimethylborate or triisopropylborate. A preferred base for the metal halogen exchange could be isopropylmagnesium chloride-lithium chloride complex in THF at low temperature.

Scheme 2 shows how one skilled in the art can combine intermediate IIa or IIb with intermediate Ic, where Y=boronate, in the case of reaction with IIa, or halide, in the case of reaction with I % to provide intermediates of general formula III. (Intermediates of general formula Ic are commercially available or can be prepared using methods well known to those skilled in the art of organic synthesis.) The transformation can be achieved by those skill in the art using transition metal catalyzed coupling of the appropriate boronate with the appropriate halide. More specifically, this transformation can be achieved using a Suzuki type coupling with PdCl$_2$(dppf)[DCM] as the catalyst and aqueous tribasic potassium phosphate as the base in solvents like 1,4-dioxane at elevated temperatures. Similar chemistry can be done with intermediate II to produce fully substituted 1,2,3-triazoles (intermediates of general formula IIa). It is necessary in these cases to take the corresponding bromo-triazole and subject it to additional palladium catalyzed coupling with alkyl or alkenyl boronates (in this case followed by olefin reduction using methods known in the art, i.e.—catalytic hydrogenation).

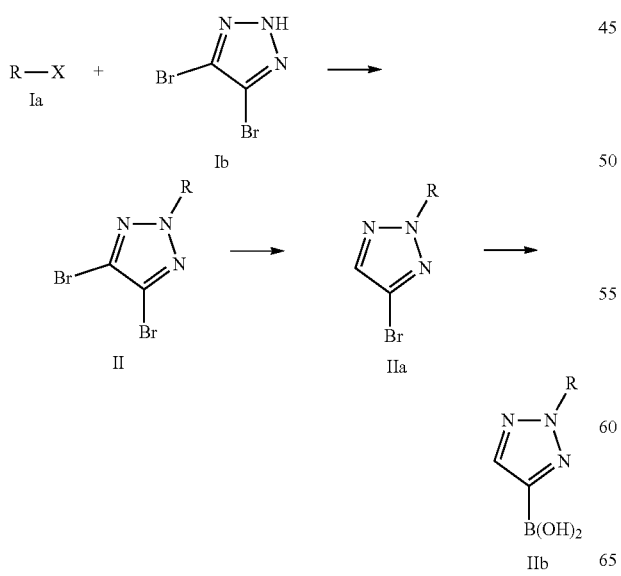

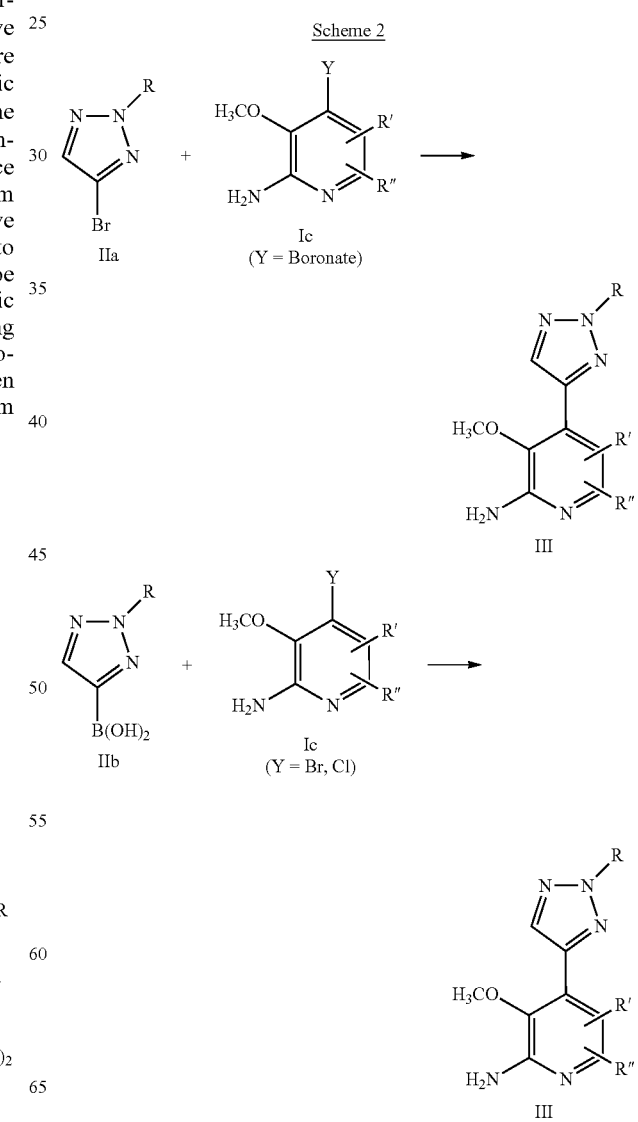

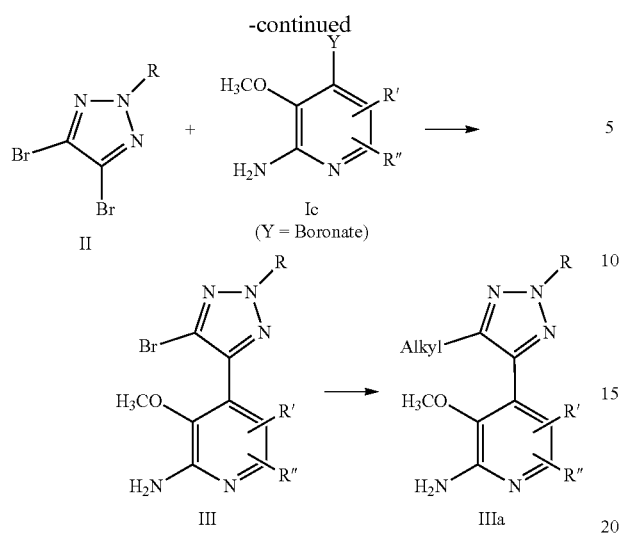

Scheme 3 shows how one skilled in the art of organic synthesis can couple intermediates of general formula Id (refer to WO 2020/086616) with amides/amines to provide intermediates of general formula IV or IVa. In particular, favorable conditions for this reaction involve employing a Buchwald type coupling, using Pd$_2$(dba)$_3$, as catalyst, xantphos as the ligand and Cs$_2$CO$_3$ as the base in 1,4-dioxane as solvent, at elevated temperatures. This catalyst/ligand/base system can be altered in ways known to those skilled in the art.

strate to produce compounds of general formula 1. The coupling of compounds of general formula IV with primary amides of general formula Ig or aromatic amines of general formula Ih, under transition metal catalyzed conditions. In particular, favorable conditions for this reaction involve employing a Buchwald type coupling, using Pd$_2$(dba)$_3$, as catalyst, xantphos as the ligand and Cs$_2$CO$_3$ as the base in 1,4-dioxane as solvent, at elevated temperatures. This catalyst/ligand/base system can be altered in ways known to those skilled in the art.

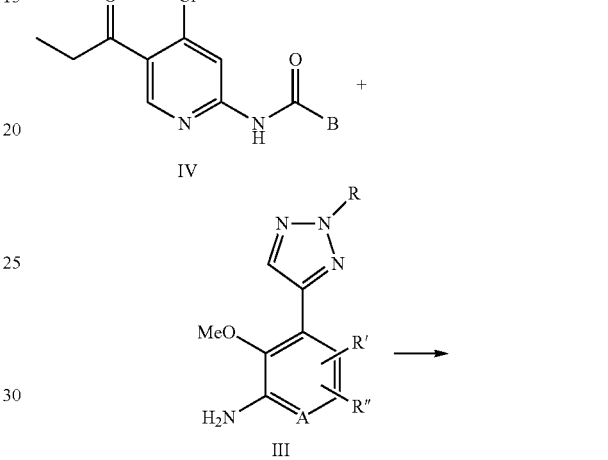

Scheme 3

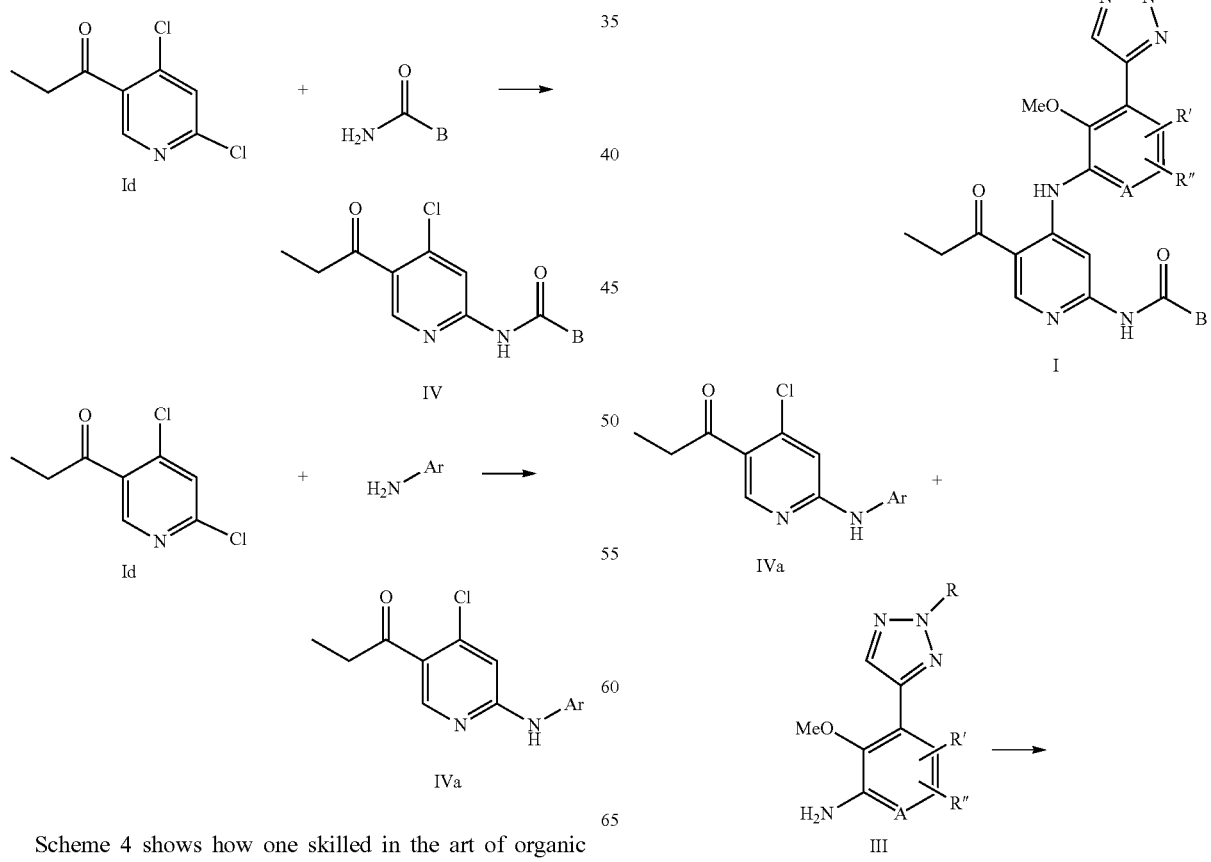

Scheme 4 shows how one skilled in the art of organic synthesis can couple compound IV to the appropriate sub-

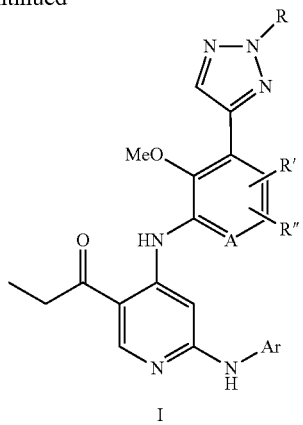

I

Preparation

All reagents purchased from commercial sources were used without further purification unless otherwise noted. All reactions involving air or moisture sensitive reagents were performed under an inert atmosphere. Proton and carbon magnetic resonance ($^1$H and $^{13}$C NMR) spectra were recorded either on a Bruker Avance 400 or a JEOL Eclipse 500 spectrometer and are reported in ppm relative to the reference solvent of the sample in which they were run. HPLC and LCMS analyses were conducted using a Shimadzu LC-10AS liquid chromatograph and a SPDUV-vis detector at 220 or 254 nm with the MS detection performed with a Micromass Platform LC spectrometer.

LCMS-Method A:

Linear gradient of 20% to 100% solvent B over 4 minutes with 0.6-minute hold at 100% B and
followed by 0.1-minute gradient to 20% B and a 0.3-minute hold at 20% B Solvent A: 5 mM Ammonium formate pH 3.3: ACN (98:02)

Solvent: B: ACN: Buffer (98:02)

Flow Rate: 1.0 ml/min

Column: Kinetex XB—C$_{18}$ (75×3.0) mm, 2.6 μm

Ultraviolet ("UV") visualization at 220 nanometers ("nm").

LCMS-Method B:

Linear gradient of 5% to 95% solvent B over 2.5 minutes with 1.5-minute hold at 95% B and
followed by 0.5-minute gradient to 5% B and a 1.5-minute hold at 5% B Solvent A: 0.1% TFA in H$_2$O Solvent: B: 0.1% TFA in ACN Flow Rate: 1.5 ml/min Column: XBridge C$_8$ (50×4.6) mm, 3.5 μm Ultraviolet ("UV") visualization at 220 nanometers ("nm").

GCMS Method:

Chromatographic column: HP-5 (30 m×320 μm×0.25 μm)

Column length 30 m, internal diameter 0.32 Mm, thickness 0.25 μm

Inlet temperature: 250° C.; Carrier gas: He. Detector temperature: 300° C.; Column flow 2 mL/min; Airflow 400 mL/min; H2 flow 40 mL/min. Heating schedule: 120° C. hold time 3 min; Then raise to 300° C. with a 40° C./min speed and hold for 2 min., source temperature: 230° C.

| Abbreviation | Meaning |
|---|---|
| ACN | Acetonitrile |
| DIPEA | Diisopropylamine |
| LiHMDS | Lithium bis(trimethylsilyl)amide |
| EtOH | Ethanol |
| EtOAc | Ethyl acetate |
| THF | Tetrahydrofuran |
| DCM | Dichloromethane |
| TBAF | Tetra-n-butylammonium fluoride |
| DMF | N,N'-Dimethylformamide |
| TFA | Trifluoroacetic acid |
| DAST | Diethylaminosulfur trifluoride |
| Tf$_2$O | Trifluoromethanesulphonic anhydride |
| dba | dibenzylideneacetone |
| Xantphos | 4,5-Bis(diphenylphosphino)-9,9-dimethylxanthene |
| dcpf | 1,1'-Bis(dicyclohexylphosphino)ferrocene |
| dppf | 1,1'-Bis(diphenylphosphino)ferrocene |
| MeOH | Methanol |
| DIC | N,N'-Diisopropylcarbodiimide |
| HPLC | high pressure liquid chromatography |
| DIAD | Diisopropyl azodicarboxylate |
| LC | liquid chromatography |
| MS | mass spectrometry |
| rt | Room temperature |
| Pd/C | palladium on carbon |
| Et | Ethyl |
| Me | Methyl |
| h | hours |
| ° C. | °Celsius |
| PBSF | Perfluorobutanesulfonyl fluoride |
| HATU | 1-[Bis(dimethylamino)methylene]-1H-1,2,3-triazolo[4,5-b]pyridinium 3-oxid hexafluorophosphate |
| DMA | dimethylacetamide |
| MW | microwave |
| AcOH | Acetic acid |
| DMAP | 4-dimethyl aminopyridine |
| Boc | Tert-butoxy carbonyl |
| AcCl | Acetyl chloride |
| min | minutes |
| MHz | megahertz |
| m-CPBA | meta-Chloroperoxybenzoic acid |

Intermediate-1:

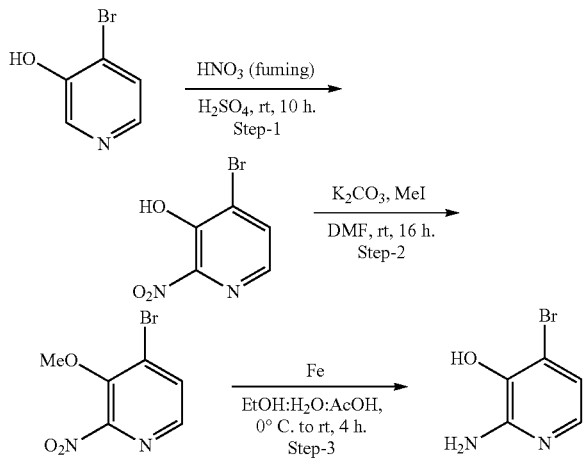

Step-1

To a −10° C. cooled 250 mL three neck round bottom flask was added 4-bromopyridin-3-ol (1.70 g, 9.77 mmol). Concentrated sulfuric acid (5 mL) was added dropwise over 10 min at −10° C. with slow stirring under N$_2$ atmosphere. The mixture was continued to stir at same temperature for 10 min, 4-bromopyridin-3-ol completely dissolves to form a clear solution. Nitric acid (fuming, 437 μL, 9.77 mmol) was added dropwise over 10 min at −10° C. The resulting mixture was allowed to attain room temperature gradually (~1.5 h) and stirred for 10 h. The reaction mixture was poured very carefully into a crushed ice (~150 g). After complete quenching, the mixture was extracted with CH$_2$Cl$_2$ (3×50 mL). The resulting organic layer was washed with saturated brine solution (30 mL), dried over anhydrous Na$_2$SO$_4$, filtered and concentrated under reduced pressure to give 4-bromo-2-nitropyridin-3-ol (1.01 g as crude). Which was used for next step without further purification.

GCMS (M) m/z: 218.0 [M]$^+$. GC retention time 7.36 min.
$^1$H-NMR (400 MHz, MeOH-d$_4$): δ 8.00 (d, J=4.8 Hz, 1H), 7.94 (d, J=4.8 Hz, 1H).

Step-2

A 250 mL three neck round bottomed flask with a stir bar was charged with 4-Bromo-2-nitropyridin-3-ol (6 g, 27.4 mmol) and DMF (100 mL). The mixture was stirred at room temperature to form a clear solution (~5 min). K$_2$CO$_3$ (7.57 g, 54.8 mmol) was added to this solution portion wise and the mixture was stirred at room temperature for 10 min. Methyl iodide (3.43 mL, 54.8 mmol) was added dropwise over 5 min and the mixture was stirred at room temperature for 16 h. The reaction mixture was quenched with water (60 mL), extracted with EtOAc (3×100 mL). The combined organic layers was washed successively with ice cold water (2×100 mL) and saturated brine solution (100 mL). The resulting organic layer was dried over anhydrous Na2SO4, filtered and concentrated under reduced pressure to afford crude product. It was purified by silica column chromatography using 0-25% EtOAc in petroleum ether as a mobile phase to afford 4-bromo-3-methoxy-2-nitropyridine as an off white solid (4.61 g, 71% yield). MS (M+1) m/z: 234.9 [M+H]t LC retention time 0.66 min [Method B]. $^1$H-NMR (400 MHz, DMSO-d$_6$): δ 8.25 (d, J=5.2 Hz, 1H), 8.20 (d, J=5.2 Hz, 1H), 3.97 (s, 3H).

Step-3

A 250 mL three neck round bottomed flask with a stir bar was charged with 4-Bromo-3-methoxy-2-nitropyridine (4.70 g, 21.5 mmol), AcOH (20 mL), EtOH (20 mL) and water (10 mL). The mixture was stirred at room temperature to form a clear solution (~5 min). The mixture cooled to 0° C. Iron powder (12.0 g, 151 mmol) was added portion wise over 10 min at 0° C. The mixture was warmed to room temperature and stirred for 4 h. The mixture was filtered through Celite bed, the Celite bed was washed with EtOAc (2×100 mL). The filtrate was sequentially washed with saturated aqueous NaHCO$_3$ (2×100 mL) and saturated brine solution (50 mL), dried over anhydrous Na$_2$SO$_4$, filtered and concentrated under reduced pressure. The crude product was purified by silica column chromatography (230-400 mesh) using 0% to 60% EtOAc in petroleum ether to afford 4-bromo-3-methoxypyridin-2-amine (3.5 g, 80% yield) as an off white solid.

MS (M+1) m/z: 205.0 [M+H]t LC retention time 0.66 min [Method B].
$^1$H-NMR (400 MHz, DMSO-d$_6$): δ 7.54 (d, J=5.2 Hz, 1H), 6.72 (d, J=5.2 Hz, 1H), 3.69 (s, 3H).

Intermediate-2

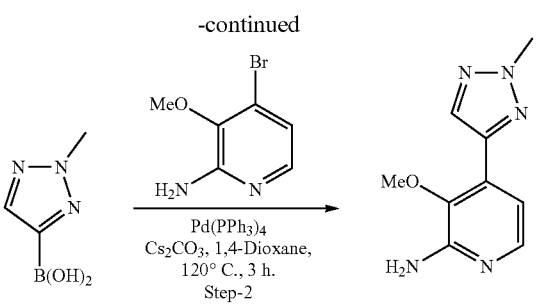

Step-1

To a stirred solution of 4-bromo-2-methyl-2H-1,2,3-triazole (5.0 g, 30.9 mmol) in THF (50 mL) was slowly added isopropylmagnesium chloride Lithium chloride complex (3.17 g, 30.9 mmol) at 0° C. The reaction was stirred for 2 hours at this temperature and then further cooled to −20° C. To this solution was then added trimethyl borate (0.64 mL, 5.7 mmol) slowly. The reaction was stirred at −20° C. for 1 h and then the reaction mixture was acidified with aqueous 1N HCl until pH~5. The resultant mixture was stirred for 10 min at 0° C. The reaction mixture was partitioned between EtOAc (50 mL) and water (50 mL). The Organic layer was collected and the aqueous layer was extracted again with EtOAc (2×100 mL) and the combined organic layers were washed with brine solution (50 mL) and then dried over anhydrous Na$_2$SO$_4$. Organic solvent was removed under pressure to obtain crude product. The resultant crude product was washed with 20 mL of n-Pentane to obtain the desired (2-methyl-2H-1,2,3-triazol-4-yl)boronic acid (2.6 g, 66.3% yield).

MS (M+1) m/z: 128.0 [M+H]$^+$. LC retention time 0.66 min [Method B].
$^1$H-NMR (400 MHz, DMSO-d$_6$): δ 8.34 (s, 2H), 7.89 (s, 1H), 4.12 (S, 3H).

Step-2

To the solution of 4-bromo-3-methoxypyridin-2-amine (0.3 g, 1.478 mmol) in 1,4-Dioxane (3 mL) and Water (0.5 ml) was added cesium carbonate (0.963 g, 2.96 mmol), (2-methyl-2H-1,2,3-triazol-4-yl)boronic acid (0.281 g, 2.216 mmol) and purged under N$_2$ gas for 5 min, followed by addition of tetrakis(triphenylphosphine)palladium(0) (0.085 g, 0.074 mmol) then subjected to heating at 120° C. for 3 h in a sealed tube. The reaction mixture was cooled to room temperature, diluted with ethylacetate (25 mL), filtered through celite pad and washed with ethylacetate (25 mL). The filtrate was sequentially washed with water (25 mL) and saturated brine solution (20 mL), dried over anhydrous Na$_2$SO$_4$, filtered and concentrated under reduced pressure. The crude residue was purified by flash column chromatography by using 0 to 30% EtOAc in petrolium ether to get the desired product 3-methoxy-4-(2-methyl-2H-1,2,3-triazol-4-yl)pyridin-2-amine (0.22 g, 72.6% yield) as yellow solid.

MS (M+1) m/z: 206.2 [M+1]$^+$. LC retention time 0.36 min [Method A].

Intermediate-3

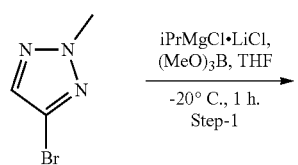

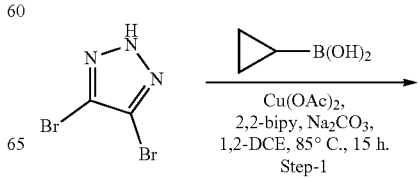

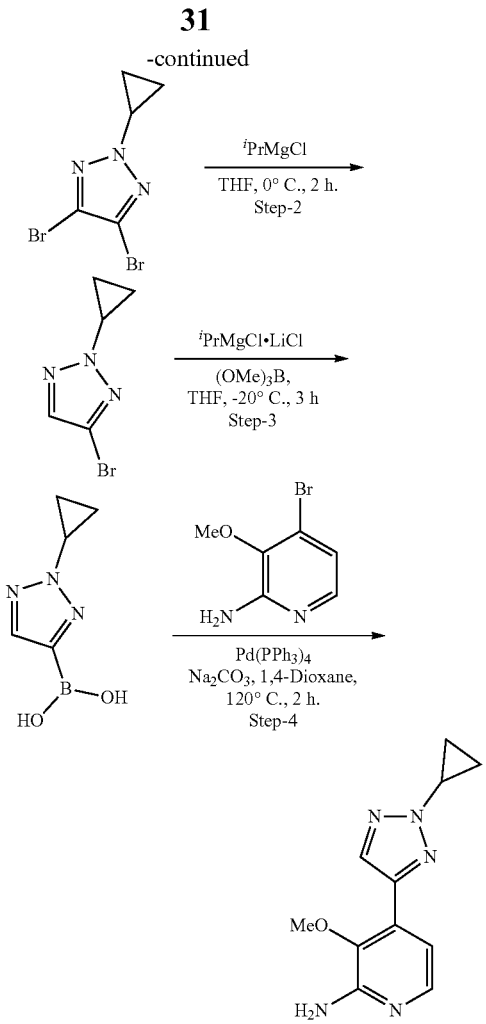

Step-1

To a stirred suspension of copper (II) acetate (29.3 g, 161 mmol) in 1,2-Dichloroethane (500 mL) in a 1000 mL three neck round bottom flask was added 2,2'-bipyridine (25.2 g, 161 mmol) and reflux the reaction mixture at 80° C. for 2 h. Cyclopropylboronic acid (34.1 g, 397 mmol), 4,5-dibromo-2H-1,2,3-triazole (30 g, 132 mmol) and sodium carbonate (28.0 g, 264 mmol) in 1,2-Dichloroethane (1000 mL) was taken in 3000 mL three neck round bottom flask then added above prepared copper (II) acetate-2,2'-bipyridine complex solution and the reaction mixture was degassed under $N_2$ gas for 5 min. The resultant reaction mixture was purged with 02 gas for 15 min and then stirred at 85° C. for 15 h. After completion, the reaction mixture was cooled to room temperature and diluted with DCM (1000 mL), filtrated through celite pad and washed thoroughly with DCM (2×500 mL). The collected filtrate was washed with aqeuous 1.5 N HCl (2×1000 mL) followed by brine solution (1000 mL), then dried over anhydrous $Na_2SO_4$ and concentrated under reduced pressure. The resultant crude residue was purified by silica gel (230-400 mesh) column chromatography using 2 to 5% EtOAc in petrolium ether to get 4,5-dibromo-2-cyclopropyl-2H-1,2,3-triazole (18 g, 46.4% yield) as a pale yellow liquid.

GCMS (M) m/z: 266.8 [M]$^+$. GC retention time 3.25 min.

$^1$H-NMR (400 MHz, DMSO-d$_6$): δ 4.01-3.98 (m, 1H), 1.38-1.34 (m, 2H), 1.16-1.11 (m, 2H).

Step-2

To a stirred solution of 4,5-dibromo-2-cyclopropyl-2H-1,2,3-triazole (18 g, 67.4 mmol) in THF (180 mL) was added isopropylmagnesium chloride (84 mL, 169 mmol) at −20° C. The reaction mixture was stirred at this temperature for 30 minutes, then allowed to warm to 0° C. and stirred for 2 h. After completion of the reaction, the reaction mixture was quenched by addition of saturated aqueous ammonium chloride solution (50 mL). The reaction mixture was extracted with EtOAc (2×500 mL) and washed with water (500 mL) followed by brine (500 mL). collected organic extract was dried over anhydrous $Na_2SO_4$ and concentrated under reduced pressure. The crude residue was purified by column chromatography on silica gel (230-400 mesh) using 5% EtOAc in petrolium ether to obtain the deisred 4-bromo-2-cyclopropyl-2H-1,2,3-triazole (12 g, 90% yield) as a pale yellow liquid.

GCMS (M) m/z: 186.9 [M]$^+$. GC retention time 2.36 min.

$^1$H-NMR (400 MHz, DMSO-d$_6$): δ 7.52 (m, 1H), 4.03-3.97 (m, 1H), 1.45-1.35 (m, 2H), 1.29-1.14 (m, 2H).

Step-3

To a stirred solution of 4-bromo-2-cyclopropyl-2H-1,2,3-triazole (12.0 g, 63.8 mmol) in THF (100 mL) was slowly added isopropylmagnesium chloride lithium chloride complex 1.3 M in THF (58.9 mL, 77 mmol) at 10° C. The reaction was stirred for 2 h at 10° C. and then further cooled to −20° C. To this solution was then added trimethyl borate (2.487 g, 23.93 mmol). The resultant reaction mixture was stirred at −20° C. for 1 h. The reaction mixture was acidified with aqueous 1N HCl until pH ~5. The resultant mixture was stirred for 10 min at 0° C. The reaction mixture was extracted with EtOAc (2×400 mL) and washed with water (200 mL), followed by brine (200 mL). Organic layer was dried over anhydrous $Na_2SO_4$ and concentrated under reduced pressure to get the crude product. The resultant crude residue was washed with 150 mL of Diethyl ether:n-Pentane (1:1) to give desired product (2-cyclopropyl-2H-1,2,3-triazol-4-yl)boronic acid (6 g, 55.3% yield) as an orange solid.

MS (M+1) m/z: 154.1 [M+1]$^+$. LC retention time 1.03 min [Method B].

$^1$H-NMR (400 MHz, DMSO-d$_6$): δ 8.34 (s, 2H), 7.89 (s, 1H), 4.14-4.10 (m, 1H), 1.21-1.19 (m, 2H), 1.15-1.08 (m, 2H).

Step-4

To a stirred solution of 4-bromo-3-methoxypyridin-2-amine (0.11 g, 0.542 mmol) in 1,4-Dioxane (3 mL) and Water (0.5 ml) was added cesium carbonate (0.353 g, 1.084 mmol), (2-cyclopropyl-2H-1,2,3-triazol-4-yl)boronic acid (0.124 g, 0.813 mmol) and purged under $N_2$ gas for 5 min, followed by addition of tetrakis(triphenylphosphine)palladium(0) (0.031 g, 0.027 mmol) then subjected to heating at 120° C. for 2 h in a sealed tube. The reaction mixture was cooled to room temperature, diluted with ethylacetate (25 mL), filtered through celite pad and and washed with ethylacetate (25 mL). The filtrate was sequentially washed with water (20 mL) and saturated brine solution (20 mL), dried over anhydrous $Na_2SO_4$, filtered and concentrated under reduced pressure to get crude product. The crude residue was purified by flash column chromatography by using 0 to 2% methanol in DCM to obtain the desired 4-(2-cyclopropyl-2H-1,2,3-triazol-4-yl)-3-methoxypyridin-2-amine (103 mg, 82% yield) as yellow solid.

MS (M+1) m/z: 232.2 [M+1]$^+$. LC retention time 1.38 min [Method A].

Intermediate-4

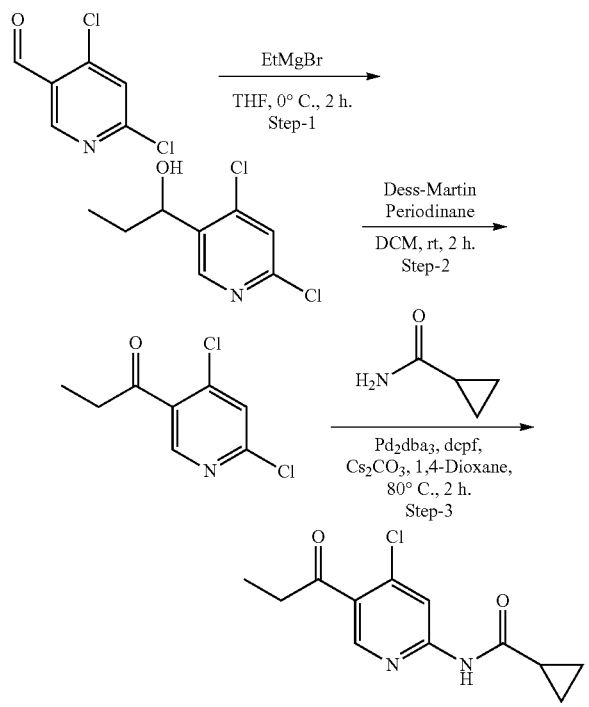

Step-1

To a stirred solution of 4,6-dichloronicotinaldehyde (8.5 g, 48.3 mmol) in THF (100 mL) was added ethylmagnesium bromide (48.3 mL, 145 mmol, 3.0 M in Diethyl ether) at 0° C. and this solution was stirred at 0° C. for 2 h. The reaction mixture was quenched with saturated aqueous $NH_4C_1$ solution (100 mL) at 0° C. and extracted with ethyl acetate (2×200 mL). Organic layer dried over anhydrous $Na_2SO_4$, filtered and concentrated under reduced pressure to obtain crude material. The crude compound was purified by silica gel flash column chromatography (20% EtOAc in hexane) to obtain 1-(4,6-dichloropyridin-3-yl) propan-1-one (4.35 g, 38.4% yield) as a pale yellow solid. MS (M+1) m/z: 206.0 [M+H]t LC retention time 1.75 min [Method B].

Step-2

To a stirred solution of 1-(4,6-dichloropyridin-3-yl)propan-1-ol (4.35 g, 21.11 mmol) in DCM (100 mL) was added Dess-Martin periodinane (17.91 g, 42.2 mmol) at 0° C. and stirred at rt for 2 h. The reaction mixture was quenched with 10% $Na_2CO_3$ solution (50 mL) and was extracted with ethyl acetate (2×200 mL). Combined organic layer dried over $Na_2SO_4$ then concentrated under reduced pressure to obtain crude material. The crude compound was purified by silica gel flash column chromatography (20% EtOAc in hexane) to obtain 1-(4,6-dichloropyridin-3-yl)propan-1-one (3.7 g, 86% yield) as a pale yellow solid.

MS (M+1) m/z: 204.0 [M+H]t LC retention time 1.44 min [Method B].

Step-3

To a stirred solution of 1-(4,6-dichloropyridin-3-yl)propan-1-one (0.2 g, 0.98 mmol) in 1,4-Dioxane (5 mL) was added cyclopropanecarboxamide (0.1 g, 1.18 mmol), cesium carbonate (0.96 g, 2.94 mmol). The reaction mixture was degassed for 5 min under $N_2$ gas, followed by addition of 1,1′-Bis(dicyclohexylphosphino)ferrocene (0.68 g, 1.18 mmol), $Pd_2dba_3$ (0.18 g, 0.196 mmol) and degassed for another 5 min. The reaction mixture was sealed and stirred at 80° C. for 2 h. The reaction mixture filtered through syringe pad and washed with ethyl acetate (50 mL). The filtrate was concentrated under reduced pressure to obtain crude material. The crude compound was purified by silica gel column chromatography (10% EtOAc in hexane) to afford N-(4-chloro-5-propionylpyridin-2-yl)cyclopropanecarboxamide (0.1 g, 40.4% yield) as a pale yellow solid.

MS (M+1) m/z: 253.0 [M+H]$^+$ LC retention time 2.25 min [Method B].

Example-1

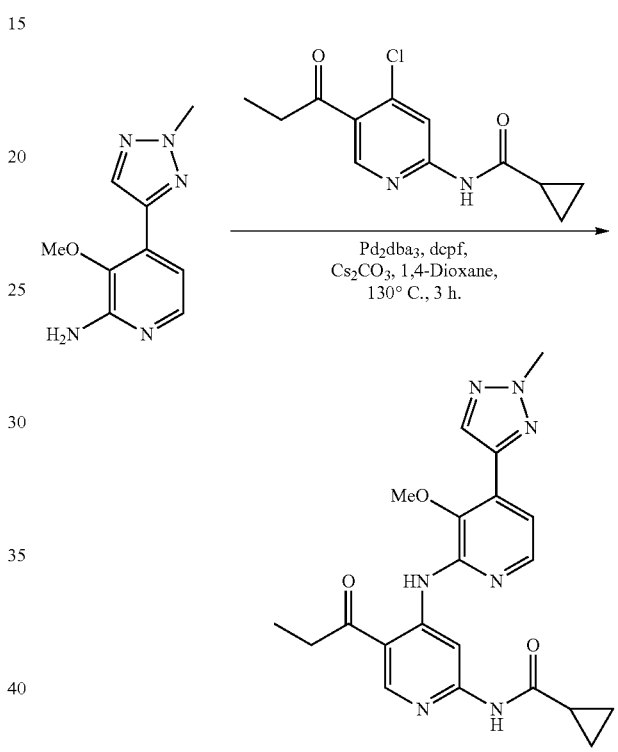

To the solution of N-(4-chloro-5-propionylpyridin-2-yl)cyclopropanecarboxamide (200 mg, 0.791 mmol) in 1,4-Dioxane (3 mL) was added cesium carbonate (516 mg, 1.583 mmol), 3-methoxy-4-(2-methyl-2H-1,2,3-triazol-4-yl)pyridin-2-amine (162 mg, 0.791 mmol) and degassed for 5 min under $N_2$ gas, followed by addition of 1,1′-Bis(diphenylphosphino)ferrocene (43.8 mg, 0.079 mmol) and $Pd_2dba_3$ (36.2 mg, 0.040 mmol). The reaction mixture stirred at 130° C. for 3 h in a sealed tube. The reaction mixture was cooled to room temperature, diluted with ethyl acetate (20 mL), filtered through celite pad and concentrated under reduced pressure. The resulting crude product was purified by flash chromatography by using 0 to 2% Methanol in DCM and triturated with diethyl ether (20 mL) to obtain the desired product N-(4-((3-methoxy-4-(2-methyl-2H-1,2,3-triazol-4-yl)pyridin-2-yl)amino)-5-propionylpyridin-2-yl)cyclopropanecarboxamide (54 mg, 15.9% yield) as off white solid.

MS (M+1) m/z: 422.0 [M+H]t LC retention time 2.29 min [Method B].

$^1$H-NMR (400 MHz, DMSO-d$_6$): δ 12.33 (s, 1H), 10.93 (s, 1H), 9.68 (s, 1H), 8.97 (s, 1H), 8.32 (s, 1H), 8.15 (d, J=5.20 Hz, 1H), 7.46 (d, J=5.20 Hz, 1H), 4.28 (s, 3H), 3.82

(s, 3H), 3.18 (q, J=7.20 Hz, 2H), 2.08-2.07 (m, 1H), 1.15 (t, J=7.20 Hz, 3H), 0.87-0.83 (m, 4H).

The following example 2 was prepared in a similar manner to the preparation of Example 1.

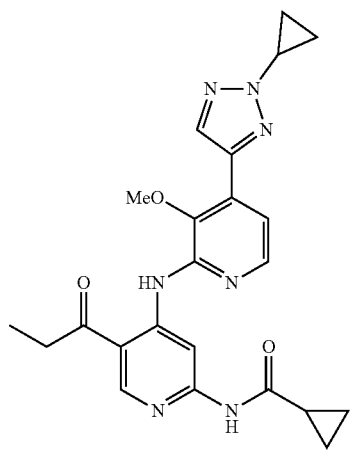 [SMILES: CCC(=O)c1cnc(NC(=O)C2CC2)cc1Nc1nccc(-c2cnn(C3CC3)n2)c1OC]

| Example No. | MW | m/z [M + H]⁺ | Rt (min) [Method] |
|---|---|---|---|
| 2 | 447.50 | 448.2 | 1.81 [B] |

Intermediate-5

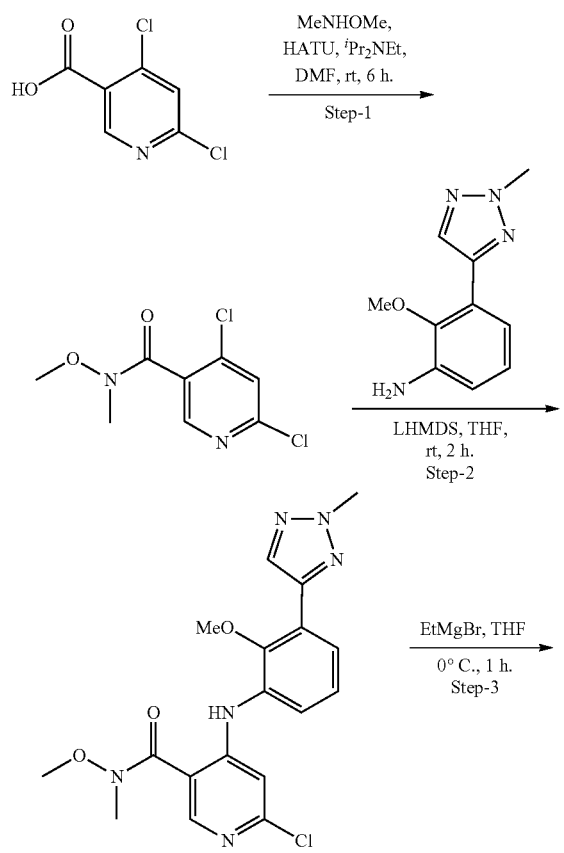

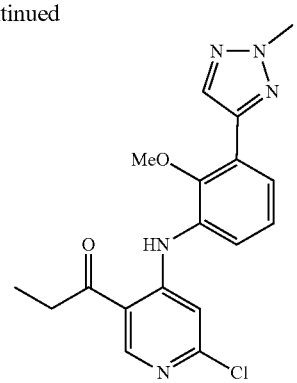

Step-1

To a stirred solution of 4,6-dichloronicotinic acid (15.0 g, 78.0 mmol) in DMF (220 mL) was added DIPEA (27.3 mL, 156.0 mmol) and HATU (44.6 g, 117.0 mmol) at 0° C. Then N,O-dimethylhydroxylamine (5.73 g, 94.0 mmol) was added in portion wise at 0° C. The reaction mixture was stirred at rt for 6 h. Cold water (150 mL) was added to the reaction mixture and extracted with Ethyl acetate (3×150 mL). Combined organic extracts were washed with brine solution (100 mL) and dried over Na₂SO₄ and concentrated under reduced pressure. The crude residue was purified by using silica gel column chromatography to obtained desired product 4,6-dichloro-N-methoxy-N-methylnicotinamide (12.5 g, 66.9% yield) as off white solid.

MS (M+1) m/z: 235.4 [M+H]⁺, LC retention time 1.36 min [Method B].

Step-2

To a stirred solution of 4,6-dichloro-N-methoxy-N-methylnicotinamide (0.8 g, 3.40 mmol) and 2-methoxy-3-(2-methyl-2H-1,2,3-triazol-4-yl)aniline (0.69 g, 3.40 mmol) in THF (20 mL) was added LiHMDS (10.21 mL, 10.21 mmol, 1 M solution in THF) at 0° C. and stirred for 2 h at rt. The reaction mixture was cooled to 0° C. and quenched with saturated aqueous NH₄Cl solution (30 mL), extracted with ethyl acetate (2×100 mL). Organic layer dried over Na₂SO₄ and then concentrated under reduced pressure to obtain crude residue. The crude compound was purified by silica gel flash column chromatography (25% EtOAc in petrolium ether) to obtain 6-chloro-N-methoxy-4-((2-methoxy-3-(2-methyl-2H-1,2,3-triazol-4-yl)phenyl)amino)-N-methylnicotinamide (0.85 g, 58.6% yield) as an orange solid.

MS (M+1) m/z: 403.1 [M+H]⁺, LC retention time 2.06 min [Method B].

Step-3

To a stirred solution of 6-chloro-N-methoxy-4-((2-methoxy-3-(2-methyl-2H-1,2,3-triazol-4-yl)phenyl)amino)-N-methylnicotinamide (0.2 g, 0.5 mmol) in THF (10 mL) and was added ethylmagnesium bromide (0.5 mL, 1.5 mmol, 3.0 M solution in diethyl ether) at 0° C. and stirred at this temperature for 2 h. The reaction mixture was quenched with saturated aqueous NH₄C₁ solution (20 mL) at 0° C. and extracted with ethyl acetate (50 mL). Organic layer dried over Na₂SO₄ then concentrated under reduced pressure to obtain crude material. The crude compound was purified by silica gel flash column chromatography (20% ethyl acetate in hexane) to afford 1-(6-chloro-4-((2-methoxy-3-(2-methyl-2H-1,2,3-triazol-4-yl)phenyl)amino)pyridin-3-yl)propan-1-one (0.14 g, 72.5% yield) as a pale yellow solid.

MS (M+1) m/z: 372.1 [M+H]⁺, LC retention time 2.17 min [Method B].

Example 3

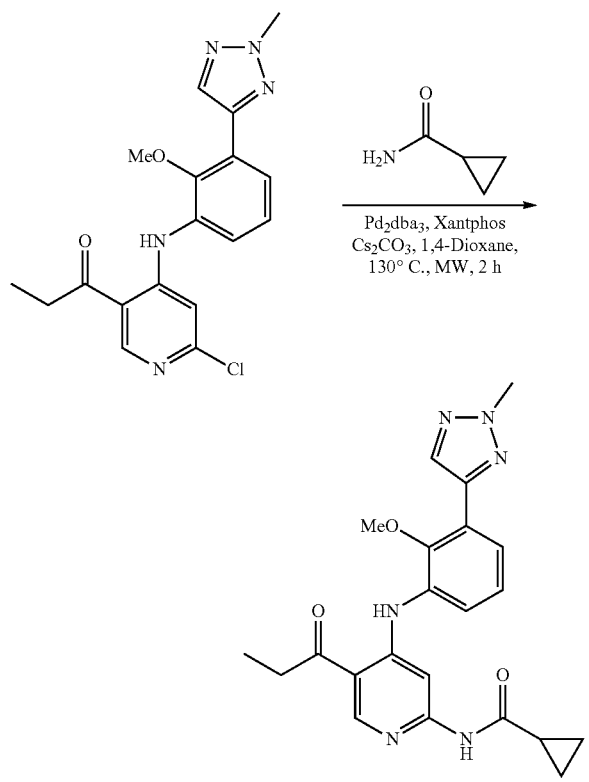

To a stirred solution of 1-(6-chloro-4-((2-methoxy-3-(2-methyl-2H-1,2,3-triazol-4-yl)phenyl)amino)pyridin-3-yl)propan-1-one (150 mg, 0.403 mmol) in 1,4-Dioxane (3 mL) was added cesium carbonate (329 mg, 1.009 mmol) and cyclopropanecarboxamide (68.7 mg, 0.807 mmol) at ambient temperature. The reaction mixture was degassed under $N_2$ for 5 minutes. $Pd_2dba_3$ (73.9 mg, 0.081 mmol) and Xantphos (46.7 mg, 0.081 mmol) were added to reaction mixture and degassed for 5 minutes. The resultant reaction mixture was stirred under MW at 130° C. for 2 h. The reaction mixture was filtered through celite pad and washed with EtOAc (50 mL) and concentrated under reduced pressure to obtain the crude product. The crude residue was purified by reverse phase preparatory HPLC to obtain N-(4-((2-methoxy-3-(2-methyl-2H-1,2,3-triazol-4-yl)phenyl)amino)-5-propionylpyridin-2-yl)cyclopropanecarboxamide (40 mg, 23.16% yield) as an off white solid.

MS (M+1) m/z: 421.0 [M+H]$^+$, LC retention time 1.18 min [Method A].

$^1$H-NMR (400 MHz, DMSO-d$_6$): δ 11.06 (s, 1H), 10.93 (s, 1H), 8.90 (s, 1H), 8.13 (s, 1H), 8.03 (s, 1H), 7.70 (d, J=7.6 Hz, 1H), 7.48 (d, J=7.6 Hz, 1H), 7.27-7.31 (m, 1H), 4.24 (s, 3H), 3.64 (s, 3H), 3.14 (q, J=7.2 Hz, 2H), 2.00-2.03 (m, 1H), 1.13 (t, J=7.2 Hz, 3H), 0.78-0.79 (m, 4H).

Intermediate-6

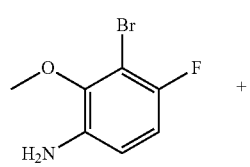 +

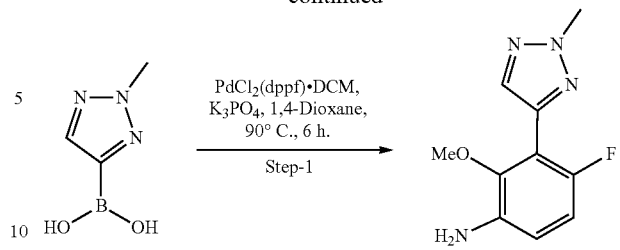

Step-1

To a stirred solution of 3-bromo-4-fluoro-2-methoxyaniline (800 mg, 3.64 mmol) and (2-methyl-2H-1,2,3-triazol-4-yl)boronic acid (554 mg, 4.36 mmol) in 1,4-Dioxane (10 mL), was added aqueous 2N $K_3PO_4$ solution (3.6 mL, 7.28 mmol) and degassed under $N_2$ for 5 min. Then added PdCl$_2$(dppf)-DCM adduct (297 mg, 0.364 mmol) to the reaction mixture and stirred at 90° C. for 6 h in a sealed tube. Reaction mixture was diluted with ethyl acetate (30 mL) and filtered through celite pad, celite pad was washed with ethyl acetate (30 mL). The filtrate was sequentially washed with water (40 mL) and saturated brine solution (40 mL), dried over anhydrous $Na_2SO_4$, filtered and concentrated under reduced pressure to get crude product. The crude residue was purified by silica gel (100-200 mesh) column chromatography using 30-35% of EtOAc in petrolium ether as an eluent to afford product desired product 4-fluoro-2-methoxy-3-(2-methyl-2H-1,2,3-triazol-4-yl)aniline (520 mg, 64.4% yield) as brown solid.

MS (M+1) m/z: 223.2 [M+H]$^+$, LC retention time 1.16 min [Method A].

Intermediate-7

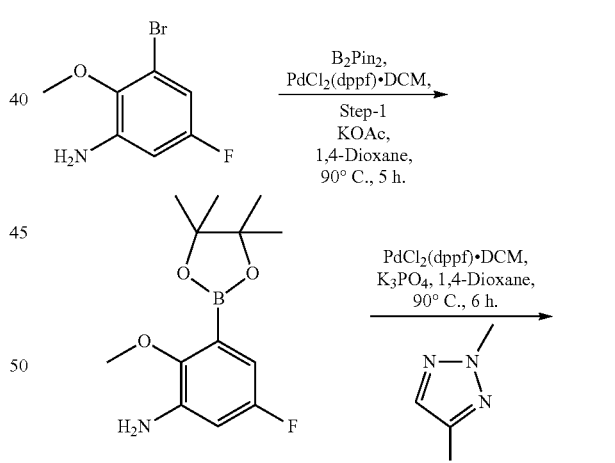

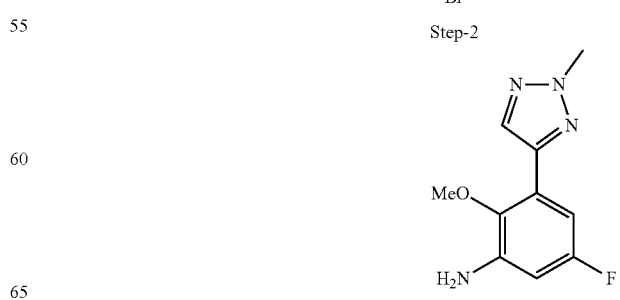

Step-1

To a stirred solution of 3-bromo-5-fluoro-2-methoxyaniline (2 g, 9.09 mmol) in 1,4-Dioxane (20 mL) in a sealed tube was added bispin (2.308 g, 9.09 mmol) and KOAc (0.892 g, 9.09 mmol) at ambient temperature. The reaction mixture was purged under $N_2$ gas for 5 min and then added the $PdCl_2$(dppf)-DCM adduct (0.742 g, 0.91 mmol). The reaction mixture stirred at 90° C. for 5 h and was cooled to room temperature. The reaction mixture was diluted with EtOAc (100 mL) and filtered through celite pad. The filtrate was washed with water (50 mL) and saturated brine solution (50 mL). Collected organic layer dried over anhydrous $Na_2SO_4$ and concentrated under reduced pressure to afford crude product. The crude residue was purified by silica gel (100-200 mesh) column chromatography using 20-25% EtOAc in petrolium ether to afford desired product 5-fluoro-2-methoxy-3-(4,4,5,5-tetramethyl-1,3,2-dioxaborolan-2-yl)aniline (2 g, 82% yield) as a white solid.

MS (M+1) m/z: 267.8 (M+H)$^+$, LC retention time 2.43 min [Method A].

Step-2

To the stirred solution of 5-fluoro-2-methoxy-3-(4,4,5,5-tetramethyl-1,3,2-dioxaborolan-2-yl)aniline (989 mg, 3.70 mmol) and 4-bromo-2-methyl-2H-1,2,3-triazole (500 mg, 3.09 mmol) in 1,4-Dioxane (10 mL) was added aqueous 2N $K_3PO_4$ solution (4.63 mL, 9.26 mmol) and purged under $N_2$ gas for 5 min. $PdCl_2$(dppf)-DCM adduct (252 mg, 0.309 mmol) was added to the reaction mixture and stirred at 90° C. for 6 h. The reaction mixture was diluted with ethyl acetate (50 mL) and washed with brine (25 mL). Organic layer collected, dried over anhydrous $Na_2SO_4$ and concentrated under reduced pressure. The crude residue was purified under silica gel (100-200 mesh) column chromatography using 35% EtOAc in petrolium ether to afford desired product 5-fluoro-2-methoxy-3-(2-methyl-2H-1,2,3-triazol-4-yl)aniline (0.6 g, 38% yield) as a brown solid.

MS (M+1) m/z: 223.0 (M+H)$^+$, LC retention time 1.95 min [Method A].

The following intermediate 8 was prepared from 3-bromo-2-methoxy-5-methylaniline in a similar manner to the preparation of intermediate 7.

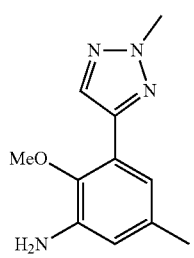 [SMILES: COc1c(N)cc(C)cc1-c1cnn(C)n1]

| Intermediate No. | MW | m/z [M + H]$^+$ | Rt (min) [Method] |
|---|---|---|---|
| 8 | 218.26 | 219.2 | 1.04 [A] |

Example 4

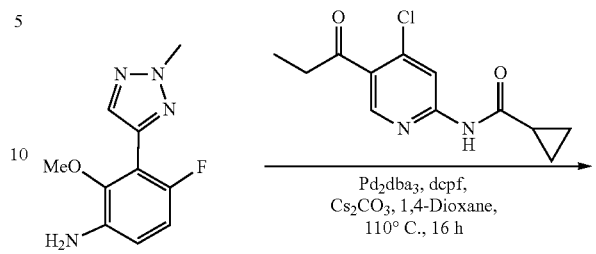

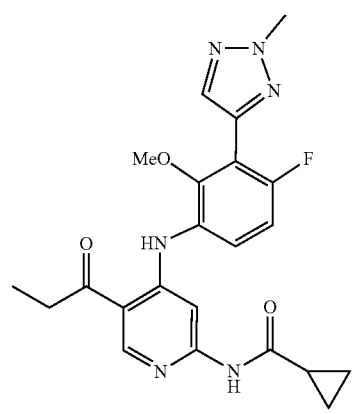

A mixture of 4-fluoro-2-methoxy-3-(2-methyl-2H-1,2,3-triazol-4-yl)aniline (376 mg, 1.691 mmol), N-(4-chloro-5-propionylpyridin-2-yl)cyclopropanecarboxamide (200 mg, 0.791 mmol), cesium carbonate (774 mg, 2.374 mmol) in 1,4-Dioxane (5 mL) was degassed by bubbling $N_2$ gas for 5 min. Then added 1,1'-Bis(dicyclohexylphosphino)ferrocene (45.8 mg, 0.079 mmol), $Pd_2dba_3$ (36.2 mg, 0.040 mmol) and the reaction mixture was degassed by bubbling $N_2$ gas for 5 min. The reaction vessel was then sealed and heated to 110° C. for 16 h. The reaction was cooled to room temperature, diluted with Ethyl acetate (20 mL), filtered through a 0.45 micron nylon filter and concentrated. The crude residue was purified by reverse phase preparatory HPLC to provide N-(4-((4-fluoro-2-methoxy-3-(2-methyl-2H-1,2,3-triazol-4-yl)phenyl)amino)-5-propionylpyridin-2-yl)cyclopropanecarboxamide (130 mg, 36.8% yield) as off white solid.

MS (M+1) m/z: 439.2 [M+H]$^+$, LC retention time 2.517 min [Method B].

$^1$H-NMR (400 MHz, DMSO-d$_6$): δ 10.92 (s, 1H), 10.85 (s, 1H), 8.88 (s, 1H), 8.02 (s, 1H), 7.84 (s, 1H), 7.53-7.50 (m, 1H), 7.24 (t, J=9.60 Hz, 1H), 4.25 (s, 3H), 3.55 (s, 3H), 3.13 (q, J=7.20 Hz, 2H), 2.02-1.99 (m, 1H), 1.11 (t, J=7.20 Hz, 3H), 0.80-0.78 (m, 4H).

The following examples (5-6) was prepared in a similar manner to the preparation of Example 4.

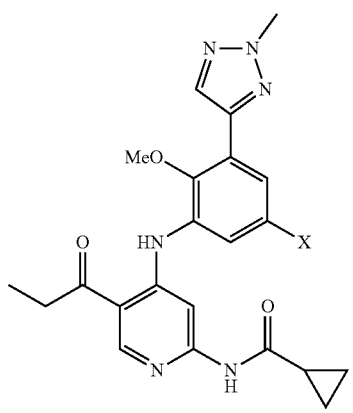

| Example No.[a] | X | MW | m/z [M + H]+ | Rt (min) [Method] |
|---|---|---|---|---|
| 5 | F | 438.46 | 439.0 | 3.11 [A] |
| 6 | CH$_3$ | 434.5 | 435.2 | 2.91 [A] |

[a]Rac-BINAP used as a lignad in the preparation, instead of dcpf.

| Example No. | $^1$H NMR |
|---|---|
| 2 | $^1$H-NMR (400 MHz, DMSO-d$_6$): δ 12.34 (s, 1H), 10.94 (s, 1H), 9.70 (s, 1H), 8.97 (s, 1H), 8.32 (s, 1H), 8.15 (d, J = 5.60 Hz, 1H), 7.47 (d, J = 5.20 Hz, 1H), 4.30-4.24 (m, 1H), 3.81 (s, 3H), 3.18 (q, J = 7.20 Hz, 2H), 2.09-2.06 (m, 1H), 1.32-1.29 (m, 2H), 1.18-1.08 (m, 5H), 0.89-0.87 (m, 4H). |
| 5 | $^1$H-NMR (400 MHz, DMSO-d$_6$): δ 11.21 (s, 1H), 11.01 (s, 1H), 8.93 (s, 1H), 8.19 (s, 1H), 8.13 (s, 1H), 7.42-7.36 (m, 2H), 4.25 (s, 3H), 3.65 (s, 3H), 3.15 (q, J = 7.20 Hz, 2H), 2.08-2.01 (m, 1H), 1.13 (t, J = 7.20 Hz, 3H), 0.86-0.80 (m, 4H). |
| 6 | $^1$H-NMR (400 MHz, DMSO-d$_6$): δ 11.15 (s, 1H), 11.05 (s, 1H), 8.87 (s, 1H), 8.11 (s, 1H), 7.65 (s, 1H), 7.60 (s, 1H), 7.30 (s, 1H), 4.24 (s, 3H), 3.61 (s, 3H), 3.15 (q, J = 7.20 Hz, 2H), 2.35 (s, 3H), 1.97 (m, 1H), 1.13 (t, J = 7.20 Hz, 3H), 0.86-0.83 (m, 4H). |

Biological Assays

The following assays are used to show the activity for compounds of the invention.

Brain Penetration In Vivo Assay

A pharmacokinetic study was performed using C57BL6 wild-type mice (n=3 per experiment) to determine brain and plasma exposure of compounds of the invention. The compound was administered orally in a solution of 5% ETHANOL; 90% PEG 300; 5% TPGS at 5 milky for a final concentration. of 10 mg/kg. Mice were euthanized 1 hour post-dose and plasma and brain were collected and frozen for analysis. Brain tissues were homogenized in a 1:1 volume of blank C57BL6 mouse plasma. Concentrations of the compound in plasma and brain homogenate were determined by LC-MS analysis.

Bidirectional Permeability Assay in Caco-2 Cells

Overview

Compounds described were tested in the Caco-2 Bidirectional Permeability Assay to assess its permeability and efflux substrate potential. Compounds (at 3 μM in triplicate) were incubated with Caco-2 cells in the assay buffer at pH 7.4 (containing 0.5% bovine serum albumin [BSA]) for 2 hours at 37° C. and then was extracted for LC-MS analysis to determine its concentration in reaction mixtures and to calculate permeability coefficient, efflux ratio, and recovery.

Materials and Methods

Caco-2 (Caucasian colon adenocarcinoma) cells were obtained from the American Type Culture Collection (Manassas, Virginia). Dulbecco's Modified Eagle's Medium (DMEM), N-2-hydroxyethylpiperazine-N'-2-ethanesulfonic acid (HEPES) buffer, nonessential amino acids, L-glutamine, penicillin-G-streptomycin, and heat-inactivated fetal bovine serum (FBS) were purchased from GIBCO/Invitrogen (Carlsbad, California). Transwell plates with 96 wells (surface area: 0.11 cm$^2$) with a 0.4-μm pore size polycarbonate membrane and low-binding transwell cluster plates, were purchased from Sigma Aldrich (Saint Louis, Missouri). Low binding 96-well plates were purchased from Corning (Corning, New York). Modified Hank's Balanced Salt Solution (MHBSS) was prepared by adjusting Hank's Balanced Salt Solution (HBSS) with HEPES to pH 7.4. HBSS, digoxin, and bovine serum albumin (BSA) were purchased from Sigma (Saint Louis, Missouri). Filtration blocks (2 mL, 96 well) were purchased from Whatman (Freiburg, Germany). All solvents were analytical grade.

Cell Preparation

Fourteen (14) to 28 days prior to assay, Caco-2 cells were seeded onto polycarbonate filter membranes in 96-well transwell plates at a density of 1.8×10$^5$ cells/cm$^2$, approximately 2.0×10$^4$ cells per well. The cells were grown in culture medium consisting of DMEM supplemented with 10% fetal bovine serum, 10 mM HEPES, 1% nonessential amino acids, 2 mM L-glutamine, 100 U/mL penicillin-G, and 100 μg/mL streptomycin. The culture medium was replaced every 3 days and the cells maintained at 37° C. in a 95% relative humidity and 5% CO$_2$ atmosphere. The cells were evaluated for tight junction formation just prior to assay (see Quality Control section below).

Compound Preparation

Compounds were solubilized to 10 mM in 100% DMSO. Following visual confirmation of complete solubilization, 10 mM stock of the compounds were plated into a 96-well plate and further serially diluted in 100% DMSO to create a 100× stock concentration of 0.3 mM. Four (4) control compounds were tested alongside described compounds, they were plated at a 100× concentration of 0.3 mM in quadruplicate.

Permeability Assessment

Compounds described were tested in triplicate in a single experiment at a final concentration of 3 μM. Cell passage used in the assay have passed QC criteria (see Quality Control section below). The study was conducted with Caco-2 cell monolayers cultured for 14 to 28 days, with cell passage numbers between 20 and 80. Assay (transport) buffer consisted of MHBSS, adjusted to pH 7.4, and 0.5% BSA. From the 100× compound plate, 8 μl, of 100% DMSO stock solution of compounds were added to 800 μl, assay buffer, mixed well, and filtered to remove any precipitate as a final preparation step before assay incubation. Targeted final test concentration of compounds described and control compounds was 3 μM. The filtrate represented the initial stock compound solution that was used as the donor solution for the assay (in both directions). The receiver solution was the assay buffer only.

Right before assay execution, each cell monolayer was washed 3 times with assay buffer to remove all traces of culture media. Permeability studies were initiated by adding 100 μl, assay buffer plus/minus compound to the apical transwell compartment and 200 μl, assay buffer plus/minus compound to the basolateral compartment of the 96-well transwell low-binding cluster plate. For apical-to-basolateral (A→B) permeability (absorptive direction), buffer containing compounds or control compounds (1x donor solution) were placed in the apical compartments (donor wells), while buffer alone was placed in the corresponding basolateral compartments (receiver wells). For basolateral-to-apical (B→A) permeability (secretive direction), buffer containing compounds or control compounds (1x donor solution) were placed in the basolateral compartments (donor wells), while buffer alone was placed in the corresponding apical compartments (receiver wells). Transwells were then incubated for 2 hours at 37° C. in a 95% relative humidity and 5% $CO_2$ atmosphere. Following incubation, 75 μl, was removed from each apical and basolateral compartment and transferred to 96-well low-binding plates that had been previously loaded with 75 μL/well of acetonitrile containing 250 nM propranolol, 250 nM diclofenac, and 500 nM tolbutamide as internal standards. The samples were subsequently analyzed by LC-MS/MS to determine concentrations of compounds described and control compounds.

Analysis of Assay Samples

The concentrations of compounds described and control compounds in the assay samples were determined by LC-MS/MS. The AB Sciex 4500/5500/6500 multiplexed systems consisted of 2 sets of binary Shimadzu 20ADvp pumps with SCL-20Avp controllers for gradient elution, and LS1 autosampler, and an AB Sciex 4500/5500/6500 triple quadrupole mass spectrometer operated under electrospray ionization (ESI) mode. To obtain the optimum SRM conditions for sample analysis, MS/MS optimization for each compound was performed using DiscoveryQuant™ (AB Sciex) featuring saturation control with 5 μM standard solutions in a mixture of methanol and water (1:1, v/v) prepared from compound stock solutions. The optimization was performed using a flow injection analysis with an injection volume of 40 μL under isocratic elution of 75% of mobile phase B (0.2% formic acid in acetonitrile) and 25% mobile phase A (0.2% formic acid in water).

A 5-μL aliquot of sample was injected and then separated on a Kinetex XB-C18, 2.6 μm, 2.1×30 mm column under a gradient elution using mobile phase consisting of A (0.2% formic acid in water) and B (0.2% formic acid in acetonitrile).

TABLE A

Bidirectional Permeability in Caco-2 Cells Assay—Mobile Phase Gradient for Sample Analysis

| Time (s) | Length (s) | Flow (mL/min) | Gradient | % A | % B |
|---|---|---|---|---|---|
| 0 | 5 | 0.7 | Step | 98 | 2 |
| 5 | 25 | 0.7 | Ramp | 2 | 98 |
| 30 | 20 | 0.7 | Step | 2 | 98 |
| 50 | 30 | 0.7 | Step | 98 | 2 |

A = 0.2% formic acid in water; B = 0.2% formic acid in acetonitrile

DiscoveryQuant™ automatically determined the optimal ionization polarity (positive or negative), precursor and product ions, declustering potential, and collision energy for compounds described and reference compounds. The optimized SRM MS/MS conditions were used for sample analysis. The peak area ratios of compounds described or control compound to internal standard were used for quantification. The peak area ratio of compound in the dosing solution was used to determine the compound concentration in the sample.

Data Analysis

The following results were reported for compounds described: permeability coefficient (Pc [nanometers per second]), efflux ratio and percent recovery.

The Pc value was calculated using the following equation:

$$Pc = \frac{C_{At} \times V_A}{S \times C_{D0} \times t}$$

Where:
$C_{At}$=concentration of the test compound in acceptor well after time t,
$V_A$=volume in acceptor well,
S=surface area of the membrane (0.11 $cm^2$),
$C_{D0}$=initial concentration of the test compound in donor well,
t=incubation time.

The efflux ratio was calculated as:

$$\text{Efflux Ratio} = \frac{Pc_{(B \to A)}}{Pc_{(A \to B)}}$$

Recovery (%) was calculated by expressing the total amount (nmol) of test compound present in the donor and receiver assay compartments at the end of incubation time (combined) as a fraction (percentage) of the total amount (nmol) of test compound added to the donor compartment before assay incubation. It was calculated using the following equation:

$$\% \text{ Recovery} = \frac{C_{Dt} \times V_D + C_{At} \times V_A}{C_{D0} \times V_D} \times 100$$

Where:
$C_{D0}$=initial concentration of the test compound in donor well,
$V_D$=volume in donor well,
$C_{Dt}$=concentration in donor well after time t,
$C_{At}$=concentration in acceptor well after time t,
$V_A$=volume in acceptor well.

Quality Control

The Caco-2 cells in one of the transwell plates used on the day of assay were evaluated for tight junction formation using trans-epithelial electrical resistance (TEER) measurement. TEER evaluation was performed using the EVOM resistance meter (World Precision Instruments, Sarasota, Florida). Each well of the transwell plate demonstrated a TEER value >600 Ω·$cm^2$, and the cell passage and all the plates of this plating batch were accepted for the assay.

Four (4) control compounds, with Pc values covering a range of permeability, were tested alongside the compounds described in each experiment. Acceptance criteria for this assay require that the results for the control compounds at 3 μM are within acceptable historical ranges. The acceptable ranges of the Pc values and efflux ratios observed historically for these 4 controls are shown in table B.

In these studies, the results for all control compounds were within their respective historical ranges. Thus, the assay data were accepted for the data analysis and evaluation of the compounds described bidirectional permeability in Caco-2 cells.

TABLE B

Bidirectional Permeability in Caco-2 Cells Assay—Historical Results for Control Compounds

| Compound | Pc (A→B) (nm/s) | Pc (B→A) (nm/s) | Efflux Ratio |
|---|---|---|---|
| Digoxin | 18 ± 7 | 265 ± 74 | 14.7 |
| Nadolol | 20 ± 9 | 25 ± 11 | 1.3 |
| Atenolol | 19 ± 8 | 27 ± 10 | 1.4 |
| Verapamil | 120 ± 20 | 160 ± 40 | 1.3 |

Values are Mean ± Standard Deviation.
Pc = permeability coefficient. A→B = apical-to-basolateral. B→A = basolateral-to-apical.

IFNα-Induced STAT Phosphorylation in Human Whole Blood

After an hour long incubation with compound, human whole blood (drawn with ACD-A as anticoagulant) was stimulated with 1000 U/mL recombinant human IFNα A/D (R&D Systems 11200-2) for 15 min. The stimulation was stopped by adding Fix/Lyse buffer (BD 558049). Cells were stained with a CD3 FITC antibody (BD 555916), washed, and permeabilized on ice using Perm III buffer (BD 558050). Cells were then stained with an Alexa-Fluor 647 pSTAT5 (pY694) antibody (BD 612599) for 60 min prior to analysis on the iQue Plus. The amount of pSTAT5 expression was quantitated by median fluorescence intensity after gating on the CD3 positive population.

TABLE 1

Potency of exemplified compounds in human whole blood assay

| Ex. # | Human Whole blood IFNa pSTAT5 IC50 (μM) | Caco-2 AB (nm/s) | Caco-2 efflux ratio |
|---|---|---|---|
| 1 | 0.037 | 663 | 0.1 |
| 2 | 0.40 | 180 | 0.2 |
| 3 | 0.46 | 183 | 0.5 |
| 4 | 0.28 | 545 | 0.4 |
| 5 | 0.71 | 258 | 0.3 |
| 6 | 0.77 | 152 | 0.3 |

TABLE 2

Comparison of CNS penetration profiles of Examples 1 and 3 with Compound A and B:

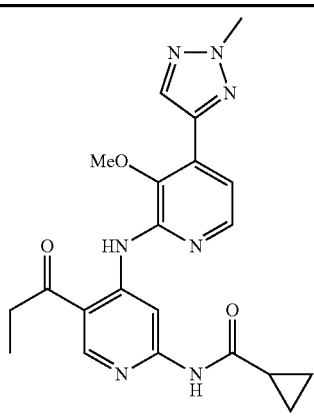

Example 1

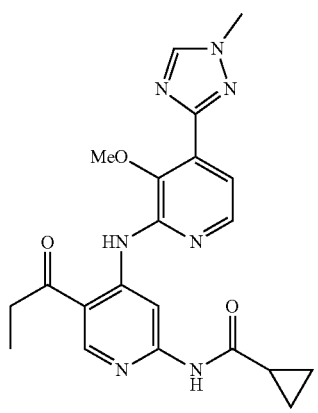 [SMILES: CCC(=O)c1cnc(NC(=O)C2CC2)cc1Nc1nccc(-c2ncn(C)n2)c1OC]

A
(Example 163 of WO 2020/086616 A)

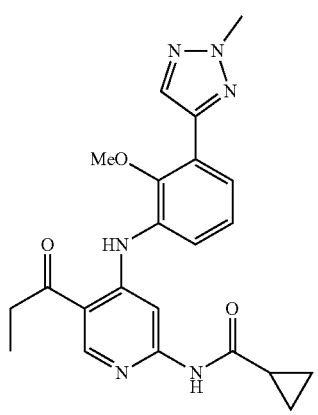 [SMILES: CCC(=O)c1cnc(NC(=O)C2CC2)cc1Nc1cccc(-c2cnn(C)n2)c1OC]

Example 3

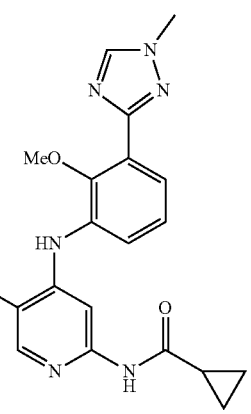

B
(Example 116 of WO 2020/086616 A)

TABLE 2-continued

Comparison of CNS penetration profiles of Examples 1 and 3 with Compound A and B:

| Compound | Ratio of exposure in brain to plasma (mouse) (1 h, 10 mpk, po) |
| --- | --- |
| Example 1 | 3.1 |
| A | 0.14 |
| Example 3 | 3.0 |
| B | 0.05 |

It has surprisingly been found that the 1,2,3-substituted triazoles compounds of the invention have a significantly higher brain to plasma ration than structurally similar 1,2,4-substituted triazole compounds. Thus, the compounds of the invention are able to penetrate the blood-brain barrier and may be useful for the treatment of certain neurological disorders.

We claim:

1. A compound of formula I

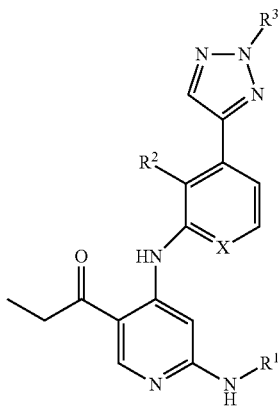

or a stereoisomer or pharmaceutically acceptable salt thereof,
wherein
X is —N— or —CH—;
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

2. The compound according to claim 1 of the formula

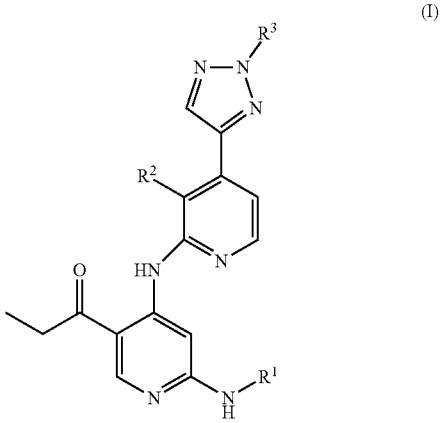

or a stereoisomer or pharmaceutically acceptable salt thereof,
wherein
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

3. The compound according to claim 1 of the formula

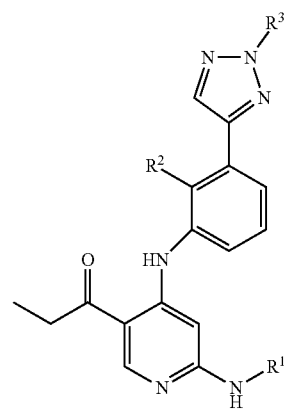

or a stereoisomer or pharmaceutically acceptable salt thereof,
wherein
$R^1$ is —C(O)$R^{1a}$;
$R^{1a}$ is $C_{3-6}$ cycloalkyl;
$R^2$ is $C_{1-6}$ alkoxy;
$R^3$ is $C_{1-6}$ alkyl or $C_{3-6}$ cycloalkyl.

4. A compound or a pharmaceutically acceptable salt thereof, selected from
N-(4-((3-methoxy-4-(2-methyl-2H-1,2,3-triazol-4-yl)pyridin-2-yl)amino)-5-propionylpyridin-2-yl)cyclopropanecarboxamide,
N-(4-((3-methoxy-4-(2-cyclopropyl-2H-1,2,3-triazol-4-yl)pyridin-2-yl)amino)-5-propionylpyridin-2-yl)cyclopropanecarboxamide,
N-(4-((2-methoxy-3-(2-methyl-2H-1,2,3-triazol-4-yl)phenyl)amino)-5-propionylpyridin-2-yl)cyclopropanecarboxamide,
N-(4-((4-fluoro-2-methoxy-3-(2-methyl-2H-1,2,3-triazol-4-yl)phenyl)amino)-5-propionylpyridin-2-yl)cyclopropanecarboxamide, N-(4-((3-fluoro-2-methoxy-3-(2-methyl-2H-1,2,3-triazol-4-yl)phenyl)amino)-5-propionylpyridin-2-yl)cyclopropanecarboxamide, and N-(4-((3-methyl-2-methoxy-3-(2-methyl-2H-1,2,3-triazol-4-yl)phenyl)amino)-5-propionylpyridin-2-yl)cyclopropanecarboxamide.

5. A pharmaceutical composition comprising one or more compounds according to claim 1 and a pharmaceutically acceptable carrier or diluent.

6. A pharmaceutical composition comprising one or more compounds according to claim 4 and a pharmaceutically acceptable carrier or diluent.

* * * * *